United States Patent [19]

Schneebaum et al.

[11] Patent Number: 5,423,830
[45] Date of Patent: Jun. 13, 1995

[54] POLYP RETRIEVAL METHOD AND ASSOCIATED INSTRUMENT ASSEMBLY

[76] Inventors: Cary W. Schneebaum, 230 Brinckerhoff Ct., Englewood, N.J. 07631; Peter J. Wilk, 185 W. End Ave., New York, N.Y. 10023

[21] Appl. No.: 88,831

[22] Filed: Jul. 7, 1993

[51] Int. Cl.⁶ .............................................. A61B 19/00
[52] U.S. Cl. .................................. 606/115; 606/110; 606/127
[58] Field of Search .............. 128/898, 749, 751, 752; 600/37; 606/1, 110, 113, 114, 115, 127, 37, 39, 45, 46, 167, 170, 191, 192, 194, 198

[56] References Cited

U.S. PATENT DOCUMENTS

| | | |
|---|---|---|
| 4,557,255 | 10/1985 | Goodman . |
| 4,997,435 | 3/1991 | Demeter ........................ 606/127 |
| 5,084,054 | 1/1992 | Bencini et al. . |
| 5,147,371 | 9/1992 | Washington .................. 606/110 |
| 5,158,561 | 10/1992 | Rydell et al. .................. 606/37 |
| 5,176,687 | 1/1993 | Hasson et al. ................ 606/114 |
| 5,190,542 | 3/1993 | Nakao et al. . |
| 5,190,561 | 3/1993 | Graber ........................... 606/127 |
| 5,192,284 | 3/1993 | Pleatman ...................... 606/110 |
| 5,196,003 | 3/1993 | Bilweis .......................... 606/1 |
| 5,215,521 | 6/1993 | Cochran et al. ............... 606/170 |
| 5,234,439 | 8/1993 | Wilk et al. .................... 606/110 |

FOREIGN PATENT DOCUMENTS

| | | | |
|---|---|---|---|
| 0499243 | 8/1992 | European Pat. Off. ............ 606/114 |
| 0537533 | 4/1993 | European Pat. Off. ............ 606/113 |
| 1683701 | 10/1991 | U.S.S.R. ............................ 606/113 |

Primary Examiner—Stephen C. Pellegrino
Assistant Examiner—Glenn Dawson
Attorney, Agent, or Firm—R. Neil Sudol; Henry D. Coleman

[57] ABSTRACT

A method for removing a polyp from inside a patient, comprises the steps of inserting an endoscopic insertion member into a patient, ejecting a cauterization loop from the insertion member, and maneuvering the insertion member and the cauterization loop from outside the patient to place the cauterization loop over a polyp inside the patient. A web member is ejected also from the endoscopic insertion member and is opened from a collapsed configuration to a substantially cup shaped opened configuration having a concave inner surface. The endoscope insertion member and the opened web member are maniipulated from outside the patient to juxtapose the concave inner surface of the web with the polyp, whereupon suction is applied to the web member to form a negative pressure zone between the web member and the polyp, thereby attaching the web member to the polyp in a vacuum seal. Then electrical current is conducted to the cauterization loop to sever the polyp from the patient. The web entrains the severed polyp for removal from the patient.

11 Claims, 2 Drawing Sheets

POLYP RETRIEVAL METHOD AND ASSOCIATED INSTRUMENT ASSEMBLY

BACKGROUND OF THE INVENTION

This invention relates to an endoscopic procedure for retrieving objects such as polyps from inside patients. This invention also relates to an associated endoscopic instrument assembly.

In a conventional polyp retrieval operation, an endoscope is inserted into an internal cavity of a patient, e.g., into the colon, and is used to visually identify and locate the polyp in the internal cavity. Upon the identification of the polyp or other growth which is to be removed, a wire extending through a tube in the biopsy channel of the endoscope is slid in the distal direction so that a cauterization loop connected to the wire is ejected from the distal end of the tube and the endoscope. The loop and the endoscope are manipulated from outside of the patient to pass the loop over the polyp or growth. The wire is then withdrawn in the proximal direction to tighten the loop around a base region or neck of the polyp. Once the loop is in contact with the base region of the polyp, an electrical current is conducted through the loop via the wire. Generally, as the loop is closed about the base region of the polyp, electrical current is transmitted through the narrowed organic tissues and thereby generates therein heat sufficiently great to cut and cauterize.

Once a polyp is severed by such a snare cauterization technique, it frequently becomes difficult to capture the polyp and retrieve it from the patient. Sometimes the cauterization loop is used in an effort to ensnare the polyp. Other capture techniques involve the use of forceps or the application of suction. In using forceps, the snare cauterization tube is removed from the biopsy channel of the endoscope and replaced with the forceps. In using suction, a vacuum is applied via a suction channel of the endoscope.

No matter which specific technique is used, the polyp frequently escapes from the capturing instrumentality and falls away into the colon (or other cavity). Especially in cases where the polyp is large, the effort and time expended in retrieving the severed polyp may rival or even exceed the effort and time required to locate and sever the polyp. In extreme cases, the endoscope must be removed without the polyp and the patient given an enema in an attempt to flush out the polyp from the colon.

Furthermore, there are numerous cases where a severed polyp is never recovered. Sometimes, the polyp is masserated during the retrieval attempt. In all such cases, the pathologist is unable to determine whether the polyp contains carcinoma in situ (localized) or infiltrative carcinoma (spread). The patient must then undergo a colon ressection, sometimes unnecessarily.

In any event, the manipulations necessary to remove a severed polyp generally increase the trauma to the patient, the expense of the surgery and the hospitalization time. There is now a long-felt need to improve the snare cauterization technique to facilitate the capture and retrieval of severed polyps.

U.S. Pat. Nos. 5,201,740 and 5,190,542 to Nakao and Wilk disclose a cauterization loop with an attached capture pocket. Such a snare assembly represents a significant advance in the art and evidently solves all of the problems inherent in polyp retrieval. However, it appears that there is some rooom in the industry for an alternative method for snare retrieval.

OBJECTS OF THE INVENTION

An object of the present invention is to provide a method for the removal of portions of internal body organs or other objects from patients.

A more specific object of the present invention is to provide such a method which may be used in conjunction with snare cauterization operations.

Another object of the present invention is to provide a technique wherein the capture and retrieval of severed polyps is facilitated.

Another, more particular, object of the present invention is to provide a polyp retrieval technique wherein trauma to the patient and time in surgery are reduced.

A further object of the present invention is to provide an instrument assembly for use in removing portions of body organs or other objects from patients.

Yet another, more particular, object of the present invention is to provide such an instrument assembly which facilitates the capture and retrieval of severed polyps and other clumps of severed body tissues from the internal cavities of patients.

Another particular object of the present invention is to provide such an instrument assembly which is simple to manufacture and therefore inexpensive.

A further particular object of the present invention is to provide such an instrument assembly which is easy to use.

An additional particular object of the present invention is to provide such an instrument assembly which is disposable. Such an instrument assembly requires no lengthy sterilization procedure and reduces the spread of infectitous diseases such as AIDS.

These and other objects will be apparent from the following descriptions.

SUMMARY OF THE INVENTION

A method for removing an object from a patient, comprises, in accordance with one conceptualization of the present invention, the steps of (a) providing a web member in a collapsed configuration inside a tubular endoscopic channel, (b) inserting, into a patient, the web member in the collapsed configuration in the tubular endoscopic channel, (c) ejecting the web member from the tubular endoscopic channel upon insertion of the web member into the patient, (d) opening the ejected web member from the collapsed configuration to a substantially cup-shaped opened configuration having a concave inner surface, (e) juxtaposing the concave inner surface of the opened web member with the object inside the patient, (f) applying suction to the juxtaposed web member to form at least a partial vacuum between the concave inner surface and the object, thereby attaching the web member to the object in a vacuum seal, and (g) removing, from the patient, the web member with the object entrained thereto by suction.

Where the object to be removed from the patient is a polyp, the method further comprises the steps of (h) providing an endoscope assembly with a cauterization loop in a folded configuration, the tubular endoscopic channel being defined by the endoscope assembly, (i) inserting the endoscope assembly into a patient, (j) ejecting the cauterization loop from the endoscope assembly at a distal end thereof, (k) opening the ejected loop from the folded configuration, (l) maneuvering the endoscope assembly and the cauterization loop from outside the patient to place the opened cauterization loop over the polyp prior to the steps of juxtaposing the web member and the polyp, applying suction and removing the web member and the entrained polyp from the patient, and (m) upon placement of the cauterization loop over the polyp and upon application of suction to the web member, conducting electrical current to the cauterization loop to sever the polyp from the patient, the removal of the polyp being executed subsequently to the conducting and catuerizing.

Where the web member is provided with a plurality of ribs having an inherent spring action, the opening of the web member is implemented by spreading the web member by the spring action.

Generally, the tubular endoscopic channel is formed by a biopsy channel of an endoscope insertion member, either within the member or in an endoscope sheath attached to the insertion member. The web member is then inserted into the patient along with the endoscope insertion member.

Alternatively, the tubular endoscopic channel is defined by a tubular member itself inserted through a biopsy channel of an endoscope assembly. The method then further comprises the steps of shifting the tubular member in a distal direction relation to the endoscope assembly and moving the web member in the distal direction relative to the tubular member.

A method for removing a polyp from inside a patient utilizes, in accordance with another conceptualization of the present invention, a web member having a plurality of ribs extending in a longitudinal direction from a base of the web member at a proximal end thereof to a mouth opening at a distal side thereof, the web member being disposed in a collapsed configuration inside a tubular endoscopic channel, the ribs having a spring bias tending to spread the web member from the collapsed configuration to a substantially cup-shaped opened configuration. The method then includes the steps of (i) inserting, into a patient, the web member in the collapsed configuration in the tubular endoscopic channel, (ii) upon completion of the step of inserting, ejecting the web member from the tubular endoscopic channel, (iii) upon ejection of the web member from the tubular endoscopic channel, opening the web member from the collapsed configuration to the cup-shaped opened configuration, (iv) manipulating the web member from outside the patient to insert the object inside the patient into the opened web member through the mouth opening, and (v) upon insertion of the object into the web member, closing the web member about the object.

Where a tubular member is provided which defines the tubular endoscopic channel, the step of closing the web member about the object includes the step of shifting the tubular member relative to the web member to institute a camming action on the ribs to press the ribs towards one another.

An endoscopic instrument assembly comprises, in accordance with the present invention, (1) an endoscope insertion member provided with a biopsy channel having a distal end, (2) a web member disposed in a collapsed configuration inside the biopsy channel, the web member having a cup shape defining a concave inner surface, (3) an ejection component operatively connected to the web member for ejecting the web member from the distal end of the biopsy channel during an endoscopic retrieval operation, (4) spreading elements operatively connected to the web member for automatically opening the web member from the collapsed configuration to the cup shape upon an ejection of the web member from the distal end of the biopsy channel, and (5) a vacuum generator operatively connected to the web member for applying suction to the web member to generate a negative pressure at the inner surface of the web member upon an ejection of the web member from the biopsy channel and upon an opening of the web member from the collapsed configuration to the cup shape.

According to another feature of the present invention, the endoscopic instrument assembly further comprises a tubular member slidably inserted inside the biopsy channel, the web member being disposed in the collapsed configuration inside the tubular member.

According to a further feature of the present invention, the spreading elements include a plurality of ribs having a spring bias tending to open the web member from the collapsed configuration to the cup shape.

In a method in accordance with the present invention, the capture and retrieval of severed polyps is facilitated. An instrument assembly in accordances with the present invention is simple to use. Accordingly, trauma to the patient and time in surgery are reduced. More specifically, time under anaesthesia with the accompanying side effects is reduced. Concomitantly, the expense of hospitalization is decreased.

DETAILED DESCRIPTION

Figure 1:
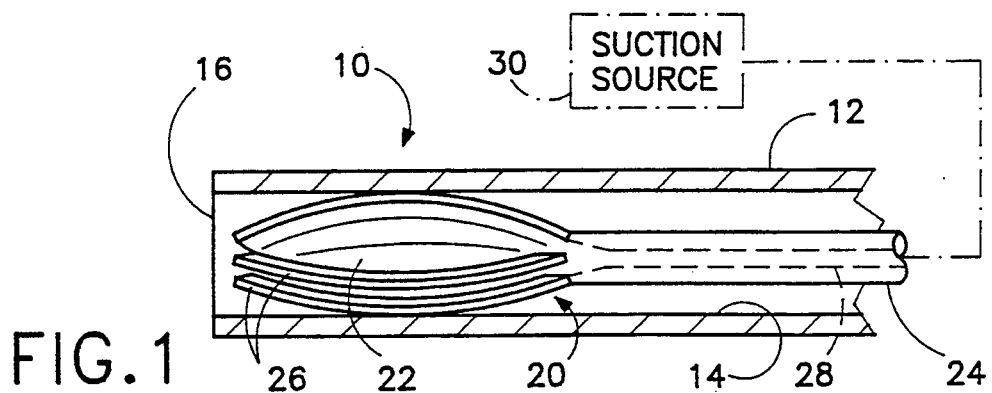
FIG. 1 is a partial schematic longitudinal cross-sectional view, on a substantially enlarged scale, of an endoscopic polyp retrieval device in accordance with the present invention, showing a cup-shaped web member in a collapsed configuration.
Figure 2:
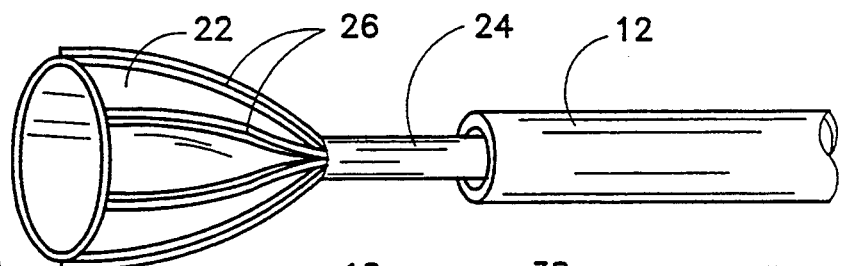
FIG. 2 is a partial schematic side perspective view of the endoscopic polyp retrieval device of FIG. 1, showing the web member in an opened configuration.

As illustrated in FIGS. 1 and 2, an endoscopic polyp retrieval device 10 comprises a tubular member 12 defining a tubular endoscopic channel 14. Tubular member 12 may be an endoscope insertion member, while endoscopic channel is a biopsy channel of the endoscope. Alternatively, tubular member 12 may be a separate instrument insertable into a biopsy channel of an endoscope.

Endoscopic channel 14 has a distal end 16. A capture component 20 is slidably disposed in tubular endoscopic channel 14. Capture component 20 includes a web member 22 disposed in a collapsed configuration inside channel 14. Web member or membrane 22 is attached at a distal end to a flexible rod 24. A plurality of longitudinally extending ribs 26 are attached to web member 22. Ribs 26 all have an internal spring bias tending to spread web member 22 into a cup-shaped opened configuration (FIG. 2) upon an ejection of the web member from tubular member 12 under the action of a distally directed stroke of rod 24.

Optionally, rod 24 is hollow, as indicated at 28, and is operatively connected at a proximal end to a suction source or vacuum pump 30, whereby web member 22 may be subjected, on a concave side, to a vacuum underpressure tending to hold an entrained object in the web member.

To remove a severed polyp PO (FIG. 3A) from inside a colon CN of a patient, an endoscope insertion member 32 is inserted into the colon. Endoscope insertion member 32 includes a fiber optic illumination guide and a fiber optic image guide represented by an illumination outlet port 34 and an imaging window 36, respectively. Endoscope insertion member 32 is further provided with a biopsy channel 38 in which tubular member 12 is slidably inserted.

Figure 3A:
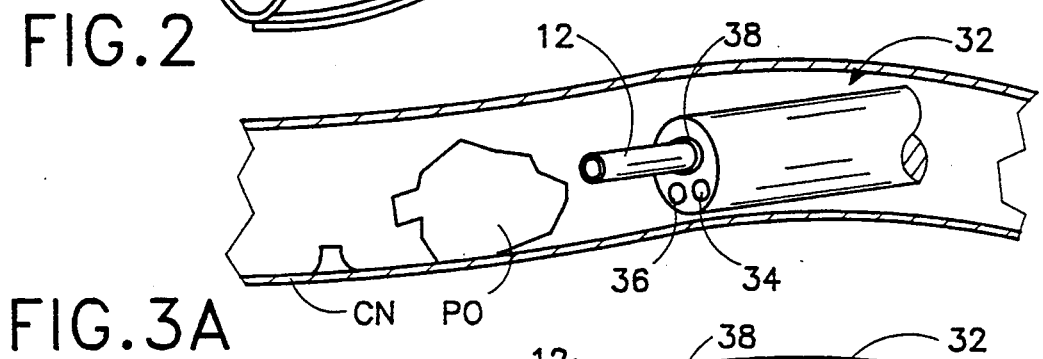
FIGS. 3A–3C are partially partial perspective views of an endoscopic polyp retrieval assembly and partially cross-sectional views of a patient's colon, showing successive steps in the use of the device of FIGS. 1 and 2 in conjunction with an endoscope in a method in accordance with the present invention.
Figure 3B:
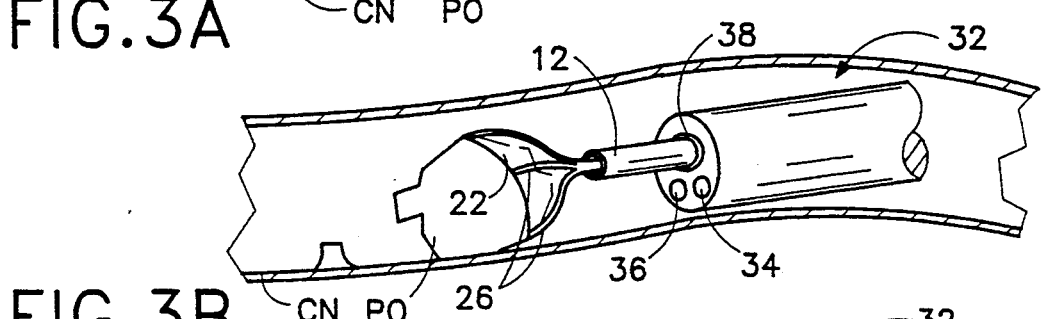
Figure 3C:
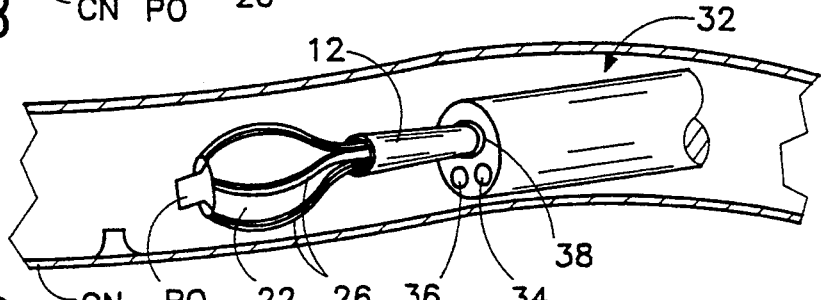

Upon the detection of polyp PO via illumination outlet port 34 and imaging window 36, tubular member 12 is pushed in a distal direction to emerge from biopsy channel 36, as illustrated in FIG. 3A. Subsequently, rod 24 (FIGS. 1 and 2) is shifted distally to eject web member 22 from channel 14. Under the action of ribs 26, web member 22 expands to the opened configuration of FIG. 2. Then endoscope insertion member 32, as well as retrieval device 10, is manipulated from outside the patient to bring the opened web member 22 into such juxtaposition with polyp PO that the polyp is inserted through a mouth of the web member and into the web member, as illustrated in FIGS. 3B and 3C. At that juncture, tubular member 12 is shifted in the distal direction to engage web member 22 and ribs 26 and to partially close the web member about the captured polyp PO, thereby effectively locking the polyp in the web member. Endoscope insertion member 32 and retrieval device 10, together with the entrained polyp PO, are removed from colon CN.

The clamping of polyp PO by ribs 26 and web member 22 under the camming closure action of tubular member 12 may be supplemented by the application of suction to the space between an inner concave surface of cup-shaped web member 22 and polyp PO. A consequent vacuum or underpressure tends to hold polyp PO to or inside web member 22 during the withdrawal of endoscope insertion member 32 from colon CN.

It is to be noted that the vacuum or negative pressure generated inside web member 22 by suction source 30 may be used exclusively to retain polyp PO in web member 22. In that event, tubular member 12 is not shifted forward to close ribs 26 and web member 22. Indeed, tubular member 12 may be omitted altogether, in which case capture component 20 is inserted directly through biopsy channel 36 without the tubular member.

Figure 4:
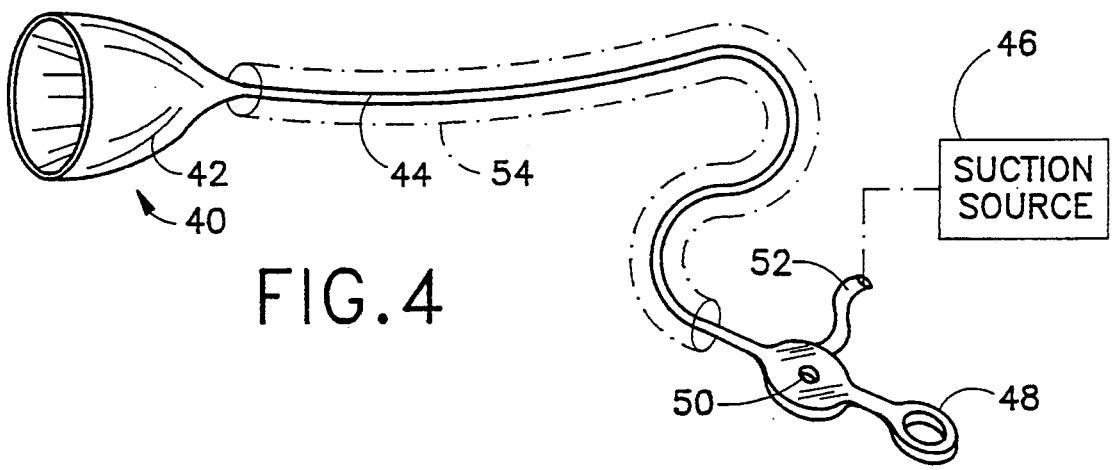
FIG. 4 is a schematic perspective view of an endoscopic polyp retrieval device for use with an endoscope in an endoscopic polyp retrieval procedure in accordance with the present invention.

FIG. 4 depicts an endoscopic polyp retrieval device 40 having a web member 42 at a distal end, a tubular shaft 44, and a suction source or vacuum generator 46 at a proximal end. The endoscopic polyp retrieval device 40 is further provided at the proximal end with a handgrip 48 for facilitating the alternate pushing and pulling of tubular shaft 44 and with an aperture 50 in a suction line 52, for enabling a user to use his or her thumb to close the pneumatic circuit extending from vacuum generator 46 to web member 42. Endoscopic polyp retrieval device 40 is insertable through a tubular member 54, which is either an endoscope insertion member or a tubular member itself insertable through an endoscope biopsy channel.

Figure 5A:
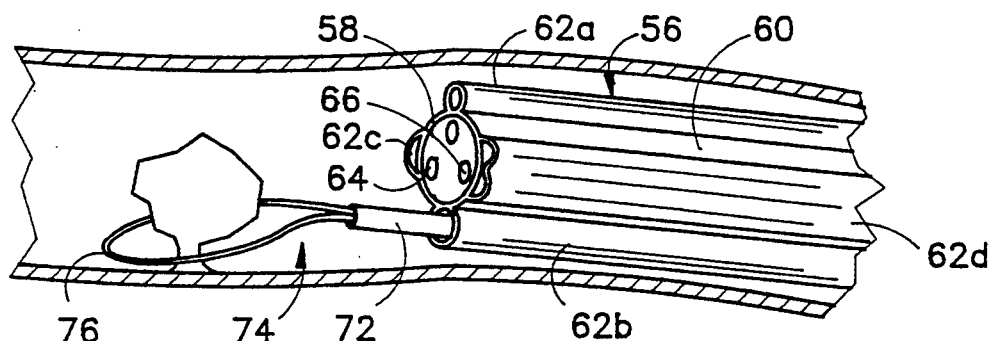
FIGS. 5A–5C are partially partial perspective views of an endoscopic polyp retrieval assembly and partially cross-sectional views of a patient's colon, showing successive steps in a method in accordance with the present invention.

As illustrated in FIG. 5A, an endoscopic polyp retrieval assesmbly 56 comprises an endoscope insertion member 58 surrounded by a sheath 60 having a plurality of expandable biopsy channels 62a, 62b, 62c, 62d. Such a sheath is described and illustrated in U.S. Pat. No. 5,217,001 the disclosure of which is hereby incorporated by reference. Endoscope-insertion member 58 also has a fiber optic illumination guide 64 and a fiber optic image guide 66.

A tubular member 68 of a endoscopic polyp retrieval device 70 (FIG. 5B) is inserted through one biopsy channel 62a, while a tubular member 72 of a cauterization snare 74 is inserted through another biopsy channel 62b. Upon the locating of a polyp POL via an image guide 66, tubular member 72 of snare 74 is pushed in the distal direction so that a distal end portion of the instrument emerges from biopsy channel 62b, as illustrated in FIG. 5A. At that juncture, a cauterization loop 76 (FIG. 5A) is ejected from a folded configuration inside tubular member 72. Endoscope insertion member 58 and tubular member 72 are then manipulated from outside the patient so as to place cauterization loop 76 over polyp POL.

Figure 5B:
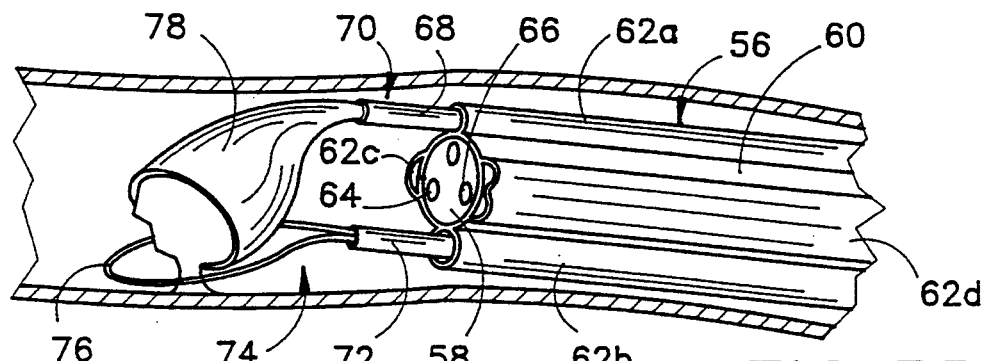

Upon the placement of cauterization loop 76 over polyp PO, tubular member 68 is shifted distally so as to partially emerge from biopsy channel 62a, as illustrated in FIG. 5B. A web member 78 is ejected from tubular member 68, opened and moved to a position in juxtaposition or engagement with polyp PO. At that point suction is applied to web member 78 to secure polyp PO to the web member, as discussed hereinabove.

Figure 5C:
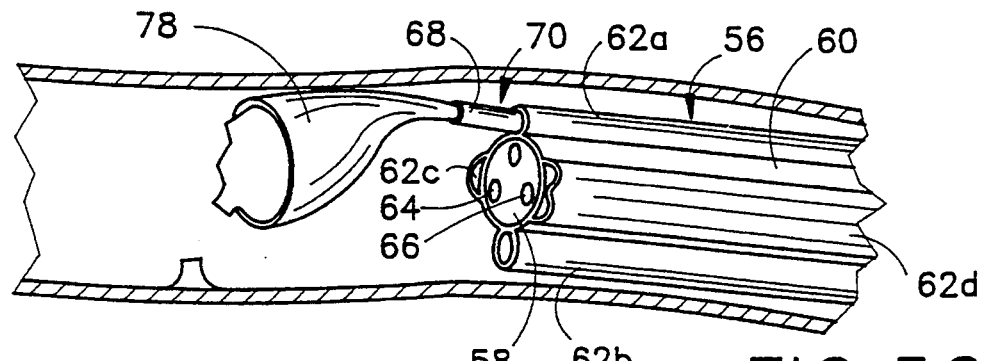

Upon the securing of polyp PO to web member 78, tubular member 72 is shifted further in the distal direction to collapse cauterization loop 76 about the base of polyp PO. Electrical current is conducted to cauterization loop 76, pursuant to conventional techniques, whereupon polyp PO is severed, as indicated in FIG. 5C. The severed polyp PO is entrained to web member 78 via suction and may be removed from the colon CLN with endoscope insertion member 58.

It is to be noted that the endoscopic polyp retrieval device embodiment of FIGS. 1 and 2 may be used in the endoscope assembly of FIGS. 5A–5C, whereby the web member can be closed through a camming action, as discussed above, either with or without the application of suction. In any case, web member 78 is provided with ribs (not designated) for facilitating the automatic opening of the web member upon ejection thereof from tubular member 68.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A method for removing an object from a patient, comprising the steps of:

providing a web member in a substantially collapsed configuration inside a tubular endoscopic channel of a flexible endoscope insertion member;

inserting, into a patient, said web member in said collapsed configuration in said tubular endoscopic channel;

upon completion of said step of inserting, ejecting said web member from said tubular endoscopic channel;

upon ejection of said web member from said tubular endoscopic channel, opening said web member from said collapsed configuration to a substantially cup-shaped opened configuration having a concave inner surface;

juxtaposing said concave inner surface of the opened web member with the object inside the patient;

upon juxtaposition of said concave inner surface with the object, applying suction to said web member to form at least a partial vacuum between said concave inner surface and the object, thereby attaching said web member to the object in a vacuum seal; and removing, from the patient, said web member with the object entrained thereto by suction.

2. The method defined in claim 1 wherein the object to be removed from the patient is a polyp, further comprising the steps of:

providing an endoscope assembly with a cauterization loop in a folded configuration, said tubular endoscopic channel being defined by said endoscope assembly;

inserting said endoscope assembly into a patient;

ejecting said cauterization loop from said endoscope assembly at a distal end thereof;

upon ejection of said cauterization loop, opening said loop from said folded configuration;

upon the opening of said cauterization loop and prior to said steps of juxtaposing, applying and removing, maneuvering said endoscope assembly and said cauterization loop from outside the patient to place said cauterization loop over the polyp; and upon placement of said cauterization loop over the polyp and upon application of suction to said web member, conducting electrical current to said cauterization loop to sever said polyp from the patient, said step of removing being executed subsequently to said step of conducting.

3. The method defined in claim 2 wherein said tubular endoscopic channel is a biopsy channel of said endoscope assembly, further comprising the step of inserting said endoscope assembly into the patient with said web member in a collapsed configuration in said biopsy channel.

4. The method defined in claim 2 wherein said tubular endoscopic channel is defined by a tubular member itself inserted through a biopsy channel of said endoscope assembly, said step of ejecting said web member including the steps of shifting said tubular member in a distal direction relative to said endoscope assembly and moving said web member in said distal direction relative to said tubular member.

5. The method defined in claim 2 wherein said web member is provided with a plurality of ribs having an inherent spring action, said step of opening said web member including the step of spreading said web member by said spring action.

6. The method defined in claim 1 wherein said tubular endoscopic channel is a biopsy channel of said endoscope insertion member, further comprising the step of inserting said endoscope insertion member into the patient.

7. The method defined in claim 1 wherein said tubular endoscopic channel is defined by a tubular member itself inserted through a biopsy channel of an endoscope assembly, further comprising the step of inserting said endoscope assembly into the patient, said step of ejecting including the steps of shifting said tubular member in a distal direction relative to said endoscope assembly and moving said web member in said distal direction relative to said tubular member.

8. The method defined in claim 1 wherein said web member is provided with a plurality of ribs having an inherent spring action, said step of opening including the step of spreading said web member by said spring action.

9. A method for removing a polyp from inside a patient, comprising the steps of:

providing an endoscope assembly including an endoscopic insertion member;

providing a cauterization loop in a first tubular channel of said endoscope assembly and a web member in a second tubular channel of said endoscope assembly;

inserting said insertion member into a patient;

ejecting said cauterization loop from said first tubular channel at a distal end of said insertion member;

maneuvering said insertion member and said cauterization loop from outside the patient to place said cauterization loop over a polyp inside the patient;

ejecting said web member from said second tubular channel;

upon ejection of said web member, opening said web member from a collapsed configuration to a substantially cup shaped opened configuration having a Concave inner surface;

upon opening of said web member and upon placement of said cauterization loop over the polyp, manipulating said insertion member and said web member to juxtapose said concave inner surface with the polyp;

upon juxtaposition of said concave inner surface with the polyp, applying suction to said web member to attach said web member to the polyp in a vacuum seal; and upon application of suction to said web member, conducting electrical current to said cauterization loop to sever said polyp from the patient.

10. A method for removing an object from inside a patient, comprising the steps of:

providing a web member having a plurality of ribs extending in a longitudinal direction from a base of said web member at a proximal end thereof to a mouth opening at a distal side thereof, said web member being disposed in a collapsed configuration inside a tubular endoscopic channel, said ribs having a spring bias tending to spread said web member from said collapsed configuration to a substantially cup-shaped opened configuration;

inserting, into a patient, said web member in said collapsed configuration in said tubular endoscopic channel;

upon completion of said step of inserting, ejecting said web member from said tubular endoscopic channel;

upon ejection of said web member from said tubular endoscopic channel, opening said web member from said collapsed configuration to said cup-shaped opened configuration;

manipulating the web member from outside the patient to insert the object inside the patient into the opened web member through said mouth opening;

upon insertion of said object into said web member, applying suction to said web member to form at least a partial vacuum between said web member and the object, thereby attaching said web member to the object in a vacuum seal;

upon insertion of said object into said web member, closing said web member about the object; and removing, from the patient, said web member with the object entrained thereto by suction.

11. The method defined in claim 10, further comprising the step of providing a tubular member defining said tubular endoscopic channel, said step of closing including the step of shifting said tubular member relative to said web member to institute a camming action on said ribs to press said ribs towards one another.

* * * * *